(12) United States Patent
Snodgrass (10) Patent No.: US 8,564,431 B2
(45) Date of Patent: Oct. 22, 2013

(54) WIRELESS MONITORING AND COMMUNICATION FOR SANITIZER DISPENSER SYSTEMS

(75) Inventor: David L. Snodgrass, Stuart, FL (US)

(73) Assignee: UltraClenz, LLC, Jupiter, FL (US)

( * ) Notice: Subject to any disclaimer, the term of this patent is extended or adjusted under 35 U.S.C. 154(b) by 543 days.

(21) Appl. No.: 12/684,019

(22) Filed: Jan. 7, 2010

(65) Prior Publication Data

US 2011/0163870 A1 Jul. 7, 2011

(51) Int. Cl.
*G08B 1/08* (2006.01)

(52) U.S. Cl.
USPC .............. 340/539.11; 340/539.1; 340/539.13; 340/10.1; 340/573.1; 340/573.4

(58) Field of Classification Search
USPC ........ 340/539.11, 539.1, 539.13, 10.1, 573.1, 340/573.4; 707/722, 769; 222/181.3, 372, 222/325
See application file for complete search history.

(56) References Cited

U.S. PATENT DOCUMENTS

| | | | | |
|---|---|---|---|---|
| 6,392,546 B1 * | 5/2002 | Smith | .......................... | 340/573.1 |
| 6,426,701 B1 * | 7/2002 | Levy et al. | .................. | 340/573.1 |
| 6,646,564 B1 * | 11/2003 | Azieres et al. | ................ | 340/679 |
| 6,727,818 B1 * | 4/2004 | Wildman et al. | .......... | 340/573.1 |
| 6,975,231 B2 * | 12/2005 | Lane et al. | ................. | 340/573.1 |
| 7,015,816 B2 * | 3/2006 | Wildman et al. | .......... | 340/573.1 |
| 7,242,307 B1 * | 7/2007 | LeBlond et al. | ........... | 340/573.1 |
| 7,423,533 B1 * | 9/2008 | LeBlond et al. | ........... | 340/572.1 |
| 7,783,380 B2 * | 8/2010 | York et al. | ..................... | 700/240 |
| 7,855,651 B2 * | 12/2010 | LeBlond et al. | ........... | 340/573.1 |
| 7,898,407 B2 * | 3/2011 | Hufton et al. | ............. | 340/539.11 |
| 2002/0135486 A1 * | 9/2002 | Brohagen et al. | .......... | 340/573.1 |
| 2002/0175182 A1 * | 11/2002 | Matthews | ........................ | 222/52 |
| 2003/0030562 A1 * | 2/2003 | Lane et al. | ................. | 340/573.4 |
| 2004/0169589 A1 * | 9/2004 | Lea et al. | ................. | 340/825.49 |
| 2005/0035862 A1 * | 2/2005 | Wildman et al. | .......... | 340/573.1 |
| 2005/0134465 A1 * | 6/2005 | Rice et al. | ................. | 340/573.1 |
| 2005/0248461 A1 * | 11/2005 | Lane et al. | ................. | 340/573.1 |
| 2005/0285740 A1 * | 12/2005 | Kubach et al. | ............. | 340/572.1 |
| 2006/0005312 A1 * | 1/2006 | Reddy et al. | ..................... | 4/668 |
| 2007/0038361 A1 * | 2/2007 | Yavitz et al. | .................. | 701/117 |
| 2007/0080801 A1 * | 4/2007 | Weismiller et al. | ...... | 340/539.13 |
| 2009/0172773 A1 * | 7/2009 | Moore | ............................. | 726/1 |
| 2009/0224907 A1 * | 9/2009 | Sinha et al. | ............. | 340/539.11 |
| 2009/0267776 A1 * | 10/2009 | Glenn et al. | ................. | 340/573.1 |
| 2009/0273477 A1 * | 11/2009 | Barnhill | ....................... | 340/573.1 |
| 2009/0299787 A1 * | 12/2009 | Barnhill | ........................... | 705/7 |
| 2010/0153374 A1 * | 6/2010 | LeBlond et al. | ............. | 707/722 |
| 2011/0063106 A1 * | 3/2011 | Snodgrass | ................ | 340/539.16 |
| 2011/0108578 A1 * | 5/2011 | Wegelin et al. | ............ | 222/181.3 |
| 2011/0163870 A1 * | 7/2011 | Snodgrass | ................ | 340/539.11 |

* cited by examiner

*Primary Examiner* — Hoi Lau (74) *Attorney, Agent, or Firm* — Lucas & Mercanti, LLP; Peter J. Phillips (57) ABSTRACT

A monitoring and communication system for sanitizer compliance monitoring, comprises a plurality of sanitizer monitoring sensors for collecting sanitize compliance data at a respective plurality of sanitizer stations, each sensor located to monitor whether a person passing through a portal has undergone a sanitization procedure, at least one hub which wirelessly receives sanitizer compliance data transmitted from said plurality of sanitizer monitoring stations, a gateway which wirelessly receives sanitizer compliance data transmitted from the hub, and a wireless cellular telephone link for transmitting the sanitizer compliance data from the gateway to a central monitoring station.

43 Claims, 5 Drawing Sheets

WIRELESS MONITORING AND COMMUNICATION FOR SANITIZER DISPENSER SYSTEMS

BACKGROUND OF THE INVENTION

The present invention relates to a sanitizer monitoring and communication system for monitoring sanitizer use by users of such systems, and for wirelessly transmitting sanitization compliance data from the dispensers to a central station, including over a cellular telephone network.

The term "sanitize" generally refers to using a sanitization product which sanitizes a person's hands, but which does not need to be washed or rinsed off with water or a towel. As used herein, unless otherwise noted, the term "sanitize" is intended to include "handwash", wherein a user washes his or her hands with soap and water.

Sanitize compliance systems collect sanitize compliance data collected by sensors at a sanitize dispenser system. The data is typically stored locally at the sanitizer dispenser. The data may be transmitted over a communications line which may be a hard-wire, such as a half-duplex RS-485 network to a central location, which may receive data from a plurality of sanitizer dispensers. The data may be analyzed at the central location, and sanitize compliance reports may be generated with a view towards insuring compliance with sanitize protocols and regulations, and to improve compliance when compliance has been found to be lacking, not optimal, or in need of improvement in some way.

SUMMARY OF THE INVENTION

In some compliance systems, monitoring data is transferred over a local network at a customer site to a monitoring station which collects and analyses the information.

Sometimes a different entity, other than the customer, collects and analyzes the data, but the data is still transferred over the customer-owned or -operated network. This may result in security issues, as the different entity doing the monitoring, should not, from the customer's perspective, have access to the entire network which includes data other than sanitize monitoring data. Also, the different entity doing the monitoring may be monitoring with a proprietary data protocol or other proprietary software application, which the different entity wishes to keep confidential from the customer.

If data is communicated over a data cable between the dispensers and a data collection device, the data cable may be expensive to install, especially for retro-fit applications. If the data collection device is a personal computer ("PC") which runs a proprietary application program at a different entity, both the customer and different entity can develop a strained relationship. If the customer opens a port in the customer's network firewall, security concerns are raised, subjecting the customer to possible security breaches by not only the different entity, but from other entities as well, seeking to hack into the customer's system through the firewall.

The present invention provides a communication arrangement which addresses some, or all, of the above concerns about cost, retro-fitting, security, and maintaining good relationships between the customer and different entity performing the data collection and compliance monitoring.

The present invention provides a reliable and cost-effective, low band-width wireless network that can be easily installed either initially, or retro-fitted in an indoor environment, and that is capable of communicating sanitize monitoring data to an off-site location, while also minimizing the burden on the customer and the customer's personnel, and existing on-site customer's network infrastructure.

As used herein, the term "portal" means a passage through which a person passes, moving from one region to another. Typically, by way of example, a portal could be a doorway, entranceway, exitway, or the like.

The invention provides a monitoring and communication system for sanitize compliance monitoring comprising: a sanitizer monitoring sensor for collecting sanitizer compliance data at a sanitizer station, said sensor located to monitor whether a person passing through a portal has undergone a sanitization procedure; and a wireless link for transmitting the sanitizer compliance data over a cellular telephone network to a central monitoring station.

The invention provides a monitoring and communication system for sanitizer compliance monitoring, comprising: a sanitizer monitoring sensor for collecting sanitizer compliance data at a sanitizer station, said sensor located to monitor whether a person entering a door has undergone a sanitization procedure; at least one hub which wirelessly receives sanitizer compliance data transmitted from said sanitizer monitoring station; a gateway which wirelessly receives sanitizer compliance data transmitted from the hub; and a wireless cellular telephone link for transmitting the sanitizer compliance data from the gateway to a central monitoring station.

The invention provides a method for monitoring and communicating sanitizer compliance data, comprising: collecting sanitize compliance data from a sanitization station having a monitoring sensor; and transmitting the collected sanitizer compliance data wirelessly over a cellular telephone network to a central monitoring station.

DESCRIPTION OF THE PREFERRED EMBODIMENT

The invention provides a monitoring and communication system for sanitize compliance monitoring comprising: a sanitizer monitoring sensor for collecting sanitizer compliance data at a sanitizer station, said sensor located to monitor whether a person passing through a portal has undergone a sanitization procedure; and a wireless link for transmitting the sanitizer compliance data over a cellular telephone network to a central monitoring station.

The monitoring sensor may transmit sanitizer compliance data to a central hub before transmission over the cellular telephone network. The wireless link may comprise a gateway which wirelessly receives the sanitizer compliance data from the monitoring sensor before transmission over the cellular telephone network. The monitoring and communication system may comprise a plurality of hubs which wirelessly communicate to a gateway before transmission over the cellular network. The monitoring and communication system may further include a remote server and database store at the central monitoring station. The monitoring and communication system may further include an internet connection at the central station to enable internet access to the remote server and database store. The monitoring and communication may include a plurality of hubs, wherein at least one hub of the plurality can receive sanitization compliance data transmitted from another hub, and retransmit the data. The sensor may comprise a passive RFID tag reader, to detect RFID tags worn by users. The system may include a sanitizer dispenser. The sensor may comprise a sanitizer dispenser and detects whether the sanitizer dispenser has dispensed sanitizer within a time period before a person is detected passing through a portal, and produces a hygiene non-compliant, portal-passage event signal if sanitizer has not been dispensed during said time period. The monitoring and communication system may include an alarm which generates a signal in response to the hygiene non-compliant, portal-passage event signal. The detector may comprise an infrared detector to detect a person. The detector may comprise a laser for producing a laser beam. The detector may be mounted along the perimeter of the portal. The monitoring and communication system may comprise a plurality of sanitizer monitoring sensors for collecting sanitizer compliance data at a respective plurality of sanitizer stations.

The invention provides a monitoring and communication system for sanitizer compliance monitoring, comprising: a sanitizer monitoring sensor for collecting sanitizer compliance data at a sanitizer station, said sensor located to monitor whether a person entering a door has undergone a sanitization procedure; at least one hub which wirelessly receives sanitizer compliance data transmitted from said sanitizer monitoring station; a gateway which wirelessly receives sanitizer compliance data transmitted from the hub; and a wireless cellular telephone link for transmitting the sanitizer compliance data from the gateway to a central monitoring station.

The invention provides a method for monitoring and communicating sanitizer compliance data, comprising: collecting sanitize compliance data from a sanitizer station having a monitoring sensor; and transmitting the collected sanitizer compliance data wirelessly over a cellular telephone network to a central monitoring station.

The method may include the step of wirelessly transmitting the sanitizer compliance data from the sanitizer station to a central hub, before transmitting the data wirelessly over the cellular network. The method may include using a gateway which wirelessly receives the sanitizer compliance data from the sanitizer monitoring sensor before transmission over the cellular telephone network. The method may include transmitting the data wirelessly over a plurality of hubs to a gateway before transmission over the cellular network. The method may include providing a remote server and database store at the central monitoring station. The method may include providing an internet connection at the central station to enable internet access to the remote server and database store. The method may include providing a plurality of hubs, wherein at least one hub of the plurality receives sanitize compliance data transmitted from another hub, and retransmits the data. The method may comprise using a passive RFID tag reader to detect RFID tags worn by users. The method may further comprise providing a sanitizer dispenser. The method may comprise detecting whether a sanitizer dispenser has dispensed sanitizer within a time period before a person is detected passing through the portal, and providing a hygiene non-compliant, portal-passage event signal if sanitizer has not been dispensed during said time period. The method may include producing an alarm signal in response to a hygiene non-compliant, portal-passage event signal. The may comprise using an infrared detector. The method may comprise locating a detector along the perimeter of the portal.

A preferred embodiment according to the invention will be described, but the invention is not limited to this embodiment.

Figure 1:
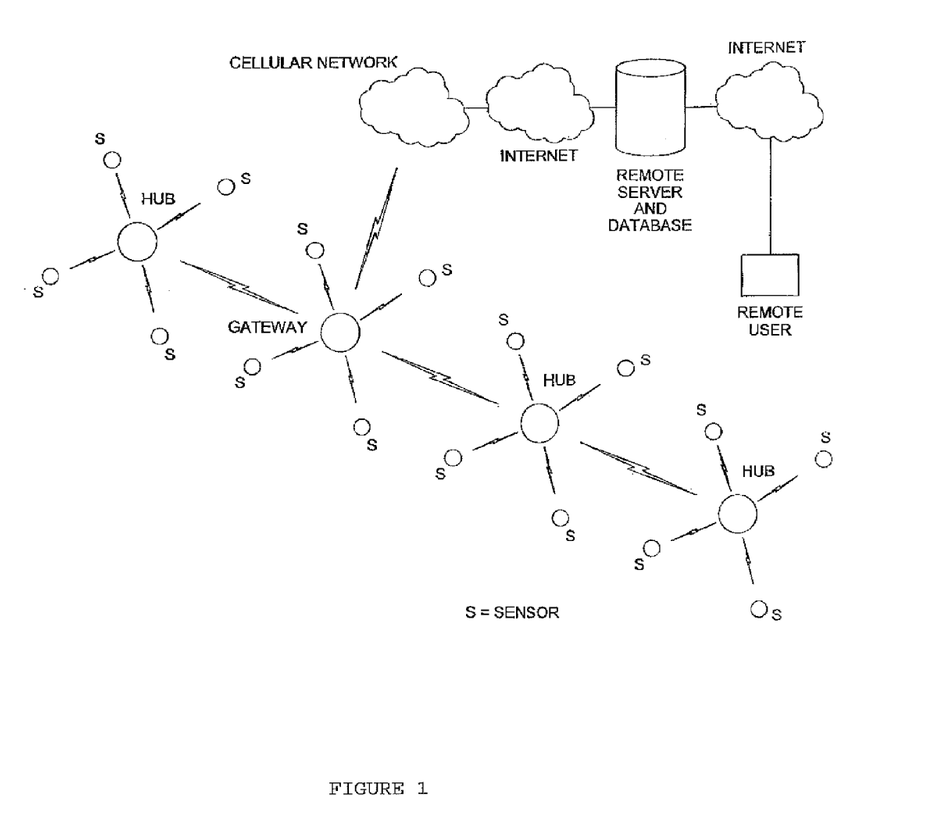
FIG. 1 is a schematic diagram showing an overall configuration of sensors, hubs, a gateway, and a cellular network.

FIG. 1 is a schematic diagram showing an overall configuration of a communication system for a sanitize compliance monitoring according to the invention. The system 10 comprises a plurality of sensors S. Each sensor S collects sanitize compliance data of a sanitize fixture, such as a sink with a dispenser which dispenses hygiene product either manually or automatically (or both) as requested, or in response to, a user's presence. Examples of sensors are disclosed in U.S. Patent Application Publications 2006/0273361 and 2006/0273915, which are incorporated herein by reference. Briefly, a sensor will collect and store sanitize compliance data, such as the identity of persons, at what times in the day such persons have performed a sanitize procedure, and whether such sanitize procedure has been correctly performed correctly according to a hygiene protocol. Variations of such compliance data may occur as understood by those skilled in the art.

The sensors may be embedded in the dispensers and may detect, and then transmit, or broadcast, data representing each sanitize dispenser activation and sanitize compliance event. Hubs H, located within reception range of a plurality of sensors, will receive the transmitted data and re-transmit the data to a gateway G, servicing a plurality of hubs H. The gateway G will then transmit the data over a cellular network CN to a remote server RS with database store. The remote server RS can be connected to the internet, and remote users RU can log onto the remote server RS with appropriate password over the internet, and retrieve the remote dispenser activation event data for processing and analysis, such as generating hygiene compliance reports.

The transmission range of the sensors S may be on the order of 50 feet, or more, to ensure that respective hub H can receive the transmitted data. The transmission of the hub H will preferably have a longer range of 100 feet or more to ensure that the gateway G will receive the transmitted data from the hubs H.

The above-described topology will provide a network at good-performance and low-cost, avoiding hand-wiring of both original and retro-fit installations.

Hubs H can be located throughout a customer facility. In addition to receiving data from sensors S, and transmitting to a gateway G, the hubs H can also, or alternatively, function as repeaters, relaying data from one hub to another to the gateway G. Good radio frequency (RF) coverage will thus be obtained, while allowing the sensors to operate at low-power levels, thereby extending battery life. By having the hubs H, which are less costly than a gateway G, serve as repeaters, savings can result by having only one gateway G at a facility, although it may be useful to have a plurality of gateways G for redundancy in case of a failure of a gateway G. Hubs H can also be provided with ranges in an over-lapping manner, so that even if a hub H becomes inoperative or loses power, the remaining hubs H can provide the transmission and repeating operations.

The gateway G uses a cellular modem to transmit the data over a cellular network. As cellular modems are relatively costly to acquire and operate, minimizing the cellular modem count to a low number, even one, will minimize installation and operating costs.

The sensor S and hubs H may operate on 900 MHz or 2.4 GHz bands, but preferably will operate at 433 MHz to avoid interference with the former two bands which are popular and crowded. Also, the 433 MHz band is better able to penetrate obstacles, like walls. As other less crowded frequency bands become available, they may be used as well. Spread spectrum transmission may be used to reduce noise and/or interference.

Each sensor S is preferably self-powered with a battery so that it can be used with existing manual and touch-free dispensers, which do not presently have power available to power the sensor. The sensor S, especially for a manual dispenser, may have a mechanical interface such as a contact closure, magnetic reed switch, or Hall-effect sensor. The preferred interface is the contact closure as this is the most reliable.

The dispensers preferably have an "expansion port". The expansion port may have an active low 3.3V logic level pin available with a 100 KΩ pull-up resistor. This pin goes active during the dispenser pump cycle which is about one second in duration. However, the manual dispenser's activation could be much shorter. To make the sensor compatible with both the manual and touch-free dispensers, the 100 KΩ pull-up resistor may be removed from the touch-free dispenser. The sensor will have a 100 KΩ pull-up resistor which makes the contact closure interface self contained and eliminates the need to add a pull-up resistor and Vcc source to the manual dispenser.

The manual dispenser is different from the touch-free because it is completely under user control. The sensor should be able to detect an activation event with a minimum duration of 100 ms. A user may not fully depress the push bar or push it very quickly causing the limit switch (contact closure) to only be closed for a short period of time. The sensor may be designed to detect up to 100 consecutive activation events in rapid succession. It is not uncommon for users to take multiple doses very rapidly. The sensor should be able to buffer up to 100 consecutive activation events in rapid succession also buffering a time offset, for each activation, based on the first activation in a rapid succession series (see Table 1). Buffering will also be preferred if one or more activations occur while the sensor is transmitting. The time offset will allow the hub to recognize the buffered activations as valid. The time offset can be added, by the hub, to the time stamp of the first activation thus resolving the time of activation for the buffered event. The time stamp will have a resolution of 1 second so it is possible that more than one valid activation will have the same time stamp. When the buffer is empty, the time offset will be cleared to 0.

Some sensors may be within range of more than one hub. This will result in multiple hubs collecting activation event data from one sensor. The remote server can detect and discard duplicate activation events before storing them in a database. More than one activation can have the same time stamp from the same sensor. To allow the server to distinguish between valid activations with the same time stamp and duplicate activations with the same time stamp, an 8-bit counter (see table 1) can be incremented with each activation. If the server sees two activations with the same time stamp from the same sensor but different counts, both activations are valid, otherwise one is a duplicate and can be discarded.

Multiple hubs may not have perfectly synchronized real-time clocks (RTC). In the case where two or more of these out of sync hubs are within range of a single sensor, each may record and time stamp the same activation event but the time stamps will not match. This creates a situation that makes it difficult for the remote server to detect duplicate activations unless an 8-bit activation count is implemented by the sensor.

TABLE 1

Possible Rapid Successive Activation Scenario

| Activation Event | Time | Time Offset | 8-Bit Counter | Time Stamp |
|---|---|---|---|---|
|  | 02:42:15.0 | 0 ms | 253 | 02:42:15 |
|  | 02:42:15.1 | 100 ms | 254 | 02:42:15 |
| 1 | 02:42:15.6 | 600 ms | 255 | 02:42:15 |
| 2 | 02:42:16.1 | 1,100 ms | 0 | 02:42:16 |
|  |  | No Activity |  |  |
| 1 | 02:55:38.5 | 0 ms | 1 | 02:55:38 |
|  |  | No Activity |  |  |
| 1 | 02:56:03.7 | 0 ms | 2 | 02:56:03 |
|  |  | No Activity |  |  |
| 1 | 03:11:26.4 | 0 ms | 3 | 03:11:26 |
| 2 | 03:11:26.8 | 400 ms | 4 | 03:11:26 |

The sensor will create an 8-byte event record for each activation that occurs (see Table 2). This record will be transmitted to the nearest hub. The event record will contain a factory programmed 32-bit device address that is unique to the sensor, an 8-bit device ID that will distinguish the current sensor from other sensors designed in the future, an 8-bit event ID to identify what kind of event occurred, an 8-bit activation count to identify duplicate event records and an 8-bit time offset to resolve activation time for multiple events occurring before they can be transmitted.

TABLE 2

8-Byte Sensor Event Record

| Device ID | Address Byte 0 | Address Byte 1 | Address Byte 2 | Address Byte 3 | Event ID | 8-Bit Activation Count | Time Offset |
|---|---|---|---|---|---|---|---|

The Address Bytes 0-3 may have a factory-programmed value between 0 and 4,294,967,296 that is unique for each sensor The Device ID may have a value from 0 to 255 that identifies the type of sensor from which the event record originated. The value for the current sensor (type 1) will be 0.

The Event ID may have a value from 0 to 255 that identifies the type of event that occurred. The current sensor (type 1) only has one event, a contact closure (dispenser activation). Sensors may have more event options such as cover open, cover closed, low battery, object blocking dispenser's IR etc. The value for a dispenser activation event will be 0.

The 8-Bit Activation Count may have a value between 0 and 255 that is incremented with each activation event. Consecutive activation events should not have the same number. When the count reaches 255, it will circle back to 0 on the following activation.

The Time Offset may have a value from 0 to 255 that, for the current activation, represents the amount of time that has passed since the first previous activation that has not yet been transmitted. The time offset value may be in 100 ms intervals i.e. 0=0 ms, 1=100 ms, 2=200 ms etc. It is possible to compress several of the above bytes into 4-bit upper and lower nibbles if the power budget requires it.

An alternative to the above-described sensors S will now be described.

A header on the dispenser's PCB may be available with power and an I²C or similar interface for an embedded sensor which would be mounted directly to the dispenser's PCB. By having a communication interface directly to the dispenser's µC, the sensor may be able to transmit not only an activation event but also low battery level, cover opened, cover closed and IR obstruction events. Dispenser configuration information such as dose setting (1, 2, 3), IR range (long, short), battery level, etc. could also be transmitted at the request of a remote user. This information could be used to remotely monitor the health and configuration of a customer's dispenser. For example, the remote server could be configured, by a remote user, to generate a warning email that would automatically be sent to a customer with a list of individual dispensers that have low batteries allowing the customer to preempt dispenser failure.

The sensor may have more communication demands made of it than the first-described sensor, and therefore, will likely consume more power. An external power source may be necessary. This means that the sensor will only be used with the touch-free dispenser and use the dispenser's D-cell batteries as its power source.

The function of the hub H is to receive, time-date stamp and buffer activation data (event records) transmitted from the surrounding sensors within its range. It then passes this data along to the nearest hub or gateway when it is requested.

The hub H should preferably be able to receive transmitted data from sensors a minimum of 50 feet away in an indoor environment. Indoor range is a subjective term so it will be assumed that the signal will only pass through a maximum of two interior walls composed of drywall and metal studs or that the signal will only pass through one exterior wall, firewall, or floor, composed of formed concrete with embedded rebar.

A circular queue may be used to buffer the last 10,000 activation events for all sensors within the hub's range. The queue will also serve as a local archive so that the remote server can request past events that may have been lost or corrupted. When the queue is full, new events will overwrite the oldest buffered events.

The hub may also function as a repeater. This wireless topology attempts to minimize the number of gateways required to send data to a remote server. To do so, hubs that are out of the gateway's range will transmit and receive data from hubs that are within their range. In turn, these hubs will transmit and receive data from hubs within their range until the data finally reaches a gateway. This forwarding of data from one hub to another will form a simple ad hoc or mesh type of network. Each hub may be able to transmit to and receive data from other hubs or a gateway a minimum of 100 feet away in an indoor environment. The signal may pass through a maximum of two interior walls composed of drywall and metal studs. It will also be assumed that the signal may only pass through one exterior wall, firewall, or floor composed of formed concrete with embedded rebar.

External power may be required due to the large distance and communication demands placed on the hub. The hub may be powered from an external 6 VDC to 12 VDC source such as a class 2 transformer.

When activation event data is requested by the gateway, the hub will send the event record as in Table 3:

TABLE 3

| | | |
|---|---|---|
| Hub Device ID | = 0-255 | - 8-bit device ID to identify type of device (100 for the hub) |
| Hub Address Byte 0 | = 0-255 | - 32-bit (bytes 0 thru 3) hub address |
| Hub Address Byte 1 | = 0-255 | |
| Hub Address Byte 2 | = 0-255 | |
| Hub Address Byte 3 | = 0-255 | |
| Event Time Stamp Hours | = 0-23 | Hours time stamp applied when event record is received from sensor |
| Event Time Stamp Minutes | = 0-59 | Minutes time stamp applied when event record is received from sensor |
| Event Time Stamp Seconds | = 0-59 | Seconds time stamp applied when event record is received from sensor |
| Event Time Stamp Month | = 0-23 | Month time stamp applied when event record is received from sensor |
| Event Time Stamp Day | = 1-31 | Day time stamp applied when event record is received from sensor |
| Event Time Stamp Year | = 0-99 | Year time stamp applied when event record is received from sensor |
| Sensor Device ID | = 0-255 | 8-Bit Device ID to identify type of device |
| Sensor Address Byte 0 | = 0-255 | 32-Bit (bytes 0 thru 3) sensor address |
| Sensor Address Byte 1 | = 0-255 | |
| Sensor Address Byte 2 | = 0-255 | |
| Sensor Address Byte 3 | = 0-255 | |
| Sensor Event ID | = 0-255 | 8-bit event ID to identify type of event that occurred |
| Sensor Activation Count | = 0-255 | 8-bit count sensor activation count |

The hub H should preferably be able to process up to 100 sensors and up to 20 sensors transmitting activation events at the same time. A hub typically processes one event at a time so a maximum time-date stamp latency of 10 seconds may be used. This should allow enough time for each individual sensor event to be processed by the hub Each hub may be equipped with a battery backed real-time clock (RTC) with a minimum accuracy of +/−5 ppm. The gateway should attempt to update each hub's RTC at least once every 24 hours to keep all hubs synchronized. When a sensor's activation event is received, the hub will do the following: (1) log the event record; (2) log the current time of the RTC to create a time-date stamp for the event; (3) check the event record's time offset byte; (4) if time offset byte is not equal to 0, adjust time-date stamp accordingly; and (5) buffer event record with time-date stamp in circular queue. Some MSP430 μCs have a built-in RTC. This would eliminate the need for the hub to deal with time offset and keep things simple.

The data in Table 3 may be in binary form using a proprietary protocol. This would make the data sufficiently difficult to decipher and eliminate the need for encryption. It is possible to compress the time-date stamp data but it is being presented in its current form to make parsing easier. Hub device ID, sensor event ID and sensor device ID may be included.

Hub installation is preferably as simple as possible. One should determine what sensors, hubs, or gateways are within range. An installer should preferably have a laptop PC available during installation. This will allow the use of a software tool that can be used to configure the hub (if necessary) and determine what devices are within range. The hub will have a half-duplex RS-485 serial port that will allow connection to the installer's PC.

The hub may be able to "discover" what other devices are within range without the need for the installer to intervene. This would be possible because each device will have a unique device ID and address combination. Discovery needs to occur within a reasonable amount of time because installers will charge by the hour.

The device may use a custom sheet metal enclosure or an ABS enclosure. Depending on size, mounting holes will be available in the PCB for fasteners. All connectors are preferably mounted at the PCB's edge for access through enclosure. Enclosure may be made of 1.5 mm steel or aluminum, with 2.50 mm from edge of PCB to outside surface of enclosure for connector placement. A right angle PCB mount SMA connector could be used so the antenna can be attached to the hub by the installer.

The invention provides a door monitoring system, such as for sanitization compliance at the entry door of a hospital room, ward, operating room, or any other passage point in any building, passageway, or structure. One example may be at the entry door of a hospital maternity ward, intensive care unit (ICU), or patient room. The door monitoring system may be used alone, or in connection with all or any part of the communication system described above.

Each person to be monitored may wear a passive RFID tag, or other unique identifier, that would identify the person at the location to be monitored. At that location, a sanitize dispenser could also be located. Even without a RFID tag reader, group monitoring, without identifying any particular individual in the group, could be accomplished. Collecting group or individual usage data may use a network to move the data from the dispenser (or its peripherals) to a database where it can be analyzed.

A wired network may be too expensive, especially if not part of an original installation at a site. While the expense may sometimes become an obstacle to installing such a system, even though sanitization requirements, and compliance with health codes, should predominate or dictate that such a system should be implemented. Especially if a system is not required, a low cost of installation may result in more frequent adoption, which will be good for sanitary reasons. Examples of locations to monitor include entrances to restaurants, schools, hospitals, museums, stores, transportation stations, government and private sector offices, and multi-tenant commercial and residence buildings.

Figure 2:
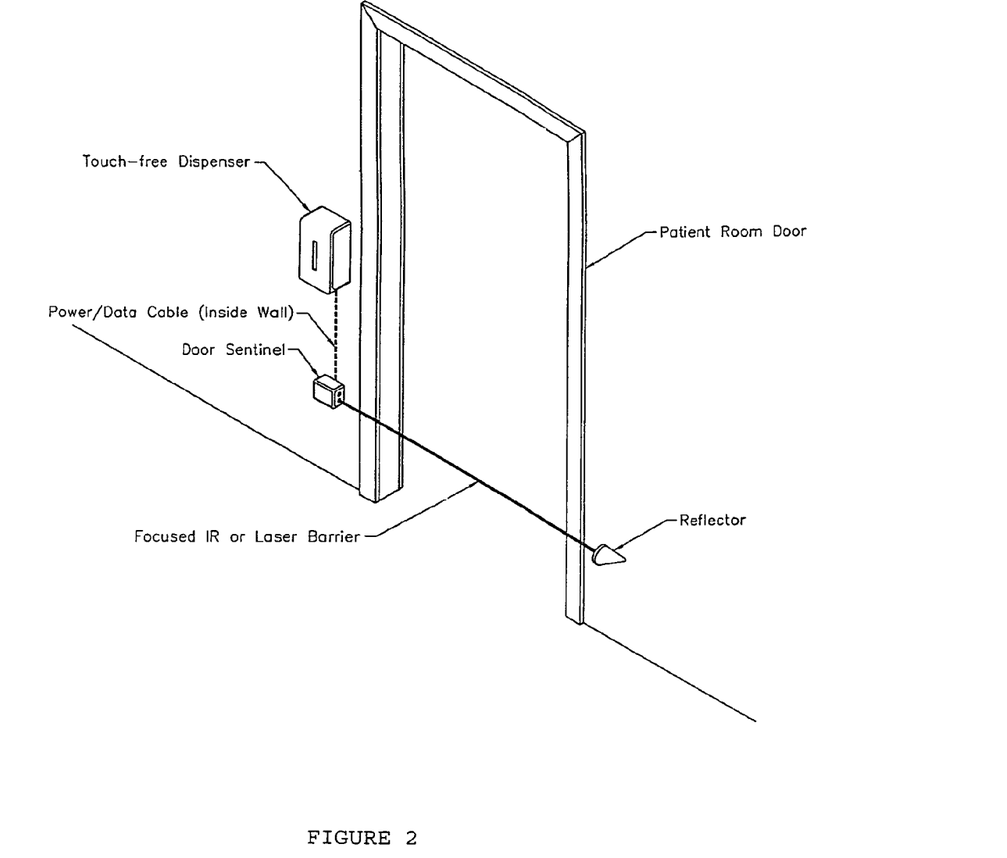
FIG. 2 shows an IR/laser based sanitizer reminder door monitor.

The system will be described using an embodiment of a hospital patient room as one example, but is not limited to this example. As shown in FIG. 2, the system uses a door sentinel which creates a barrier across a patient room doorway, which barrier will be deactivated for a period of time after hand sanitizer is dispensed from a dispenser mounted next to the doorway, allowing hygiene compliant room entry. If hand sanitizer is not dispensed prior to room entry, the barrier will not be deactivated and the system will sound an audible alarm or alert if the barrier is breached. This will indicate a hygiene noncompliant room entry event. The system will serve as a reminder to reinforce good hand hygiene habits in a hospital environment.

The system may optionally be connected to a network that will allow time and date stamped compliant and noncompliant events to be transmitted to a database for group level analysis. The network could be a wired network or a wireless network, including the wireless network described above.

Figure 3:
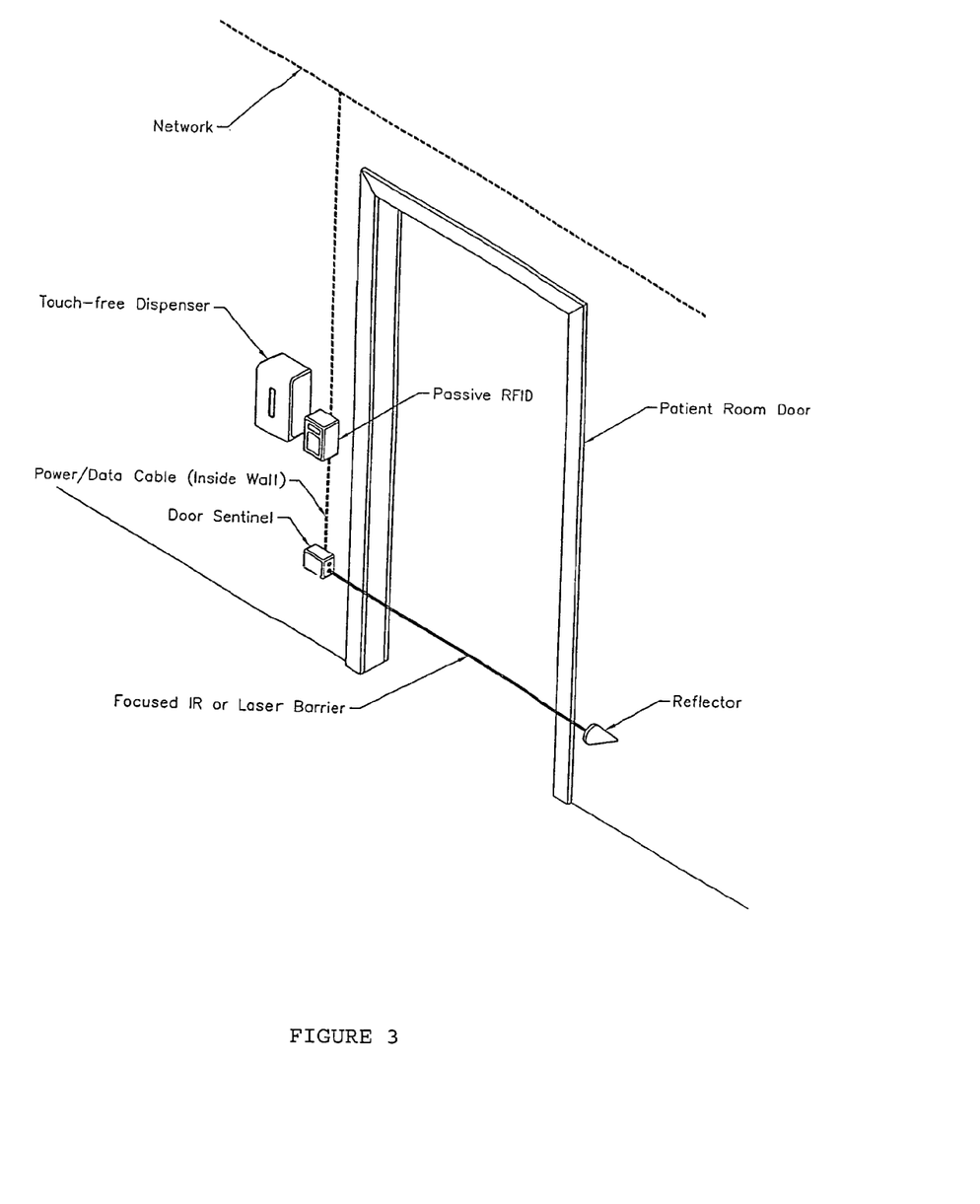
FIG. 3 shows an IR/laser based sanitizer wash door monitor with individual ID and wired network connection.

FIG. 3 shows a system that may be provided with a means of identifying an individual user whose user identification number will also be transmitted along with a time and date stamped event to a database for individual level analysis. The network could be based on RS-485 topology, but it could be expanded to Ethernet, Wi-Fi, ZigBee or ultimately a proprietary RF based network. A proprietary RF network would likely reduce installation cost and thus make the system more appealing to customers.

The system can use any one of a number of detectors to identify an individual, including infrared, ultrasonic, passive RFID, laser, LED, just to name a few. A passive RFID reader would be easy to implement and most hospital personnel already carry passive RFID cards. Eventually, active RFID could be implemented or even RF or RF/IR based badge.

FIG. 3 shows an IR/laser based hand wash door monitor with individual ID and wired network connection. The entire system may be battery powered, which would be advantageous, as it may be expensive to provide external power in a hospital environment or other potential locations. The dispenser could have D-cell batteries, would provide power to the other system components, i.e. the door sentinel and RFID reader (FIGS. 2 and 3). This will make battery replacement very easy for hospital service staff. A power/data cable could act as a buss to distribute the power to the other system components. In the case of a simple reminder system (FIG. 2) or group monitoring system, a single cable from the dispenser to the door sentinel would be sufficient to provide a connection. For an individual monitoring system, two cables may be required; one from the dispenser to the RFID reader and one from the RFID reader to the door sentinel. In either case, these wires could be run inside the wall and should not pose an installation issue. Because the installation could be made outside of the patient room, special air born precautions will likely be necessary.

Figure 4:
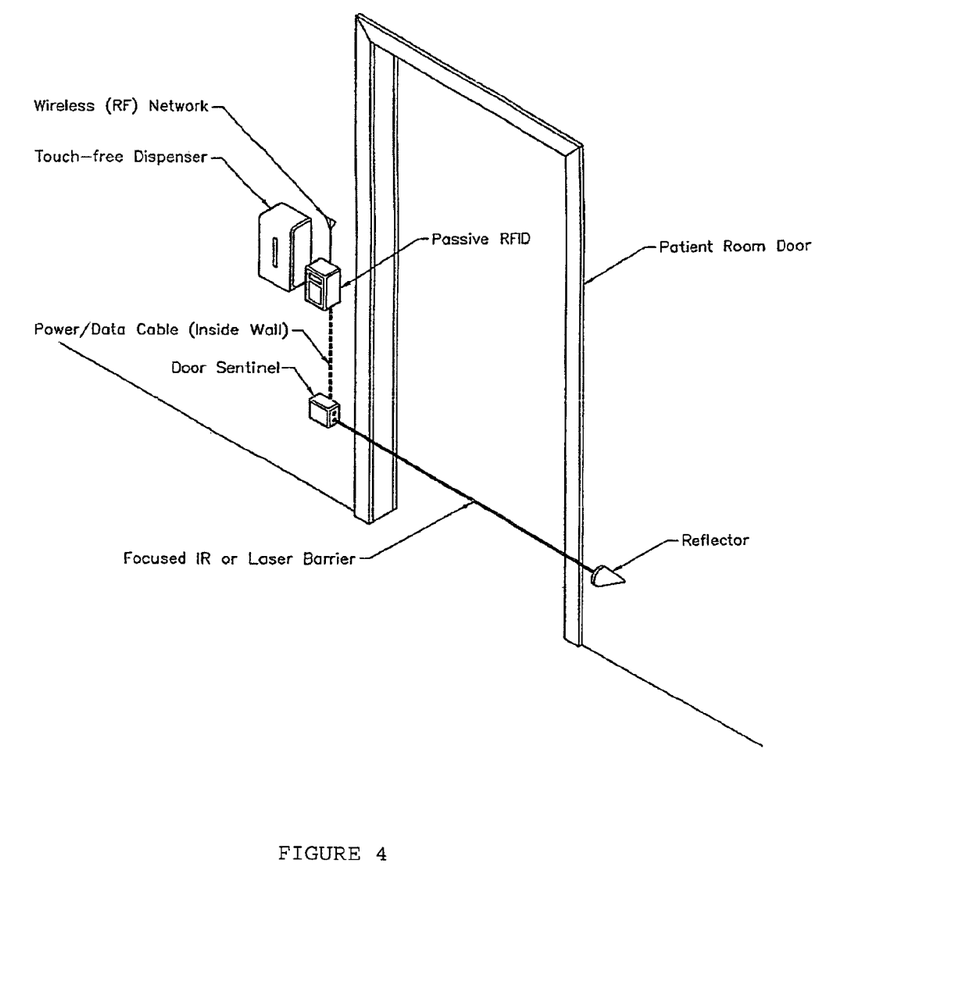
FIG. 4 shows a system with an IR or laser beam emitting from a door sentinel to create a barrier across the patient room door, with individual ID and wireless network connection.

FIGS. 2 thru 4 show a system with an IR or laser beam emitting from the door sentinel to create a barrier across the patient room door. This beam is reflected back to the door sentinel by a retro reflector (or something similar). For a battery power system, power could be conserved by modulating the beam with a duty cycle that will be the best compromise between power usage and detection accuracy. When the beam is enabled, the door sentinel will look for an object, presumably a person, breaking the beam as they walk through the doorway. If the beam is broken, the door sentinel's CPU will perform some analysis. If the CPU is satisfied that the beam was broken by a person entering the patient room without sanitizing their hands, it will sound an audible alarm and log the event with a time and date stamp. It will then transmit the event to the network at the soonest possible opportunity.

FIG. 4 shows an IR/laser based hand wash door monitor with individual ID and wireless network connection. For an TR beam to cross a 4 foot wide doorway and return may require a lens to focus the beam at the reflector. To cover the distance, the IR LED may need a current in excess of 500 mA. Even though the TED will only be on for a short period of time (possibly 500 µs) it will consume substantially greater average current then some existing dispenser IR LEDs which could mean shorter battery life for the dispenser. Most patient room doors are 4 feet wide or less but doorways over 6 feet in width are also used in hospitals. To cover larger doorways, the IR LED may need even more power. If the dispenser's batteries are powering the door sentinel, one may wish to use a lower power arrangement.

One arrangement would be to use a laser diode mounted on one side of the door about 6 inches above the floor pointing at a retro reflector at the other side of the door. Laser diodes are available with built-in lenses and only draw 20 mA to 30 mA at full power. The door sentinel may be equipped with the reflector mounted on a pair of gimbals to allow precise adjustment in both the X and Y axis.

If mounted close to the floor, someone may accidentally (or intentionally) bump or hit the reflector which may knock the laser out of alignment and render the system inoperable until it is realigned. Another possible arrangement is a PIR (Passive Infrared) sensor which detects IR (heat) radiated from the human body having a wavelength of about 10 µm.

Figure 5:
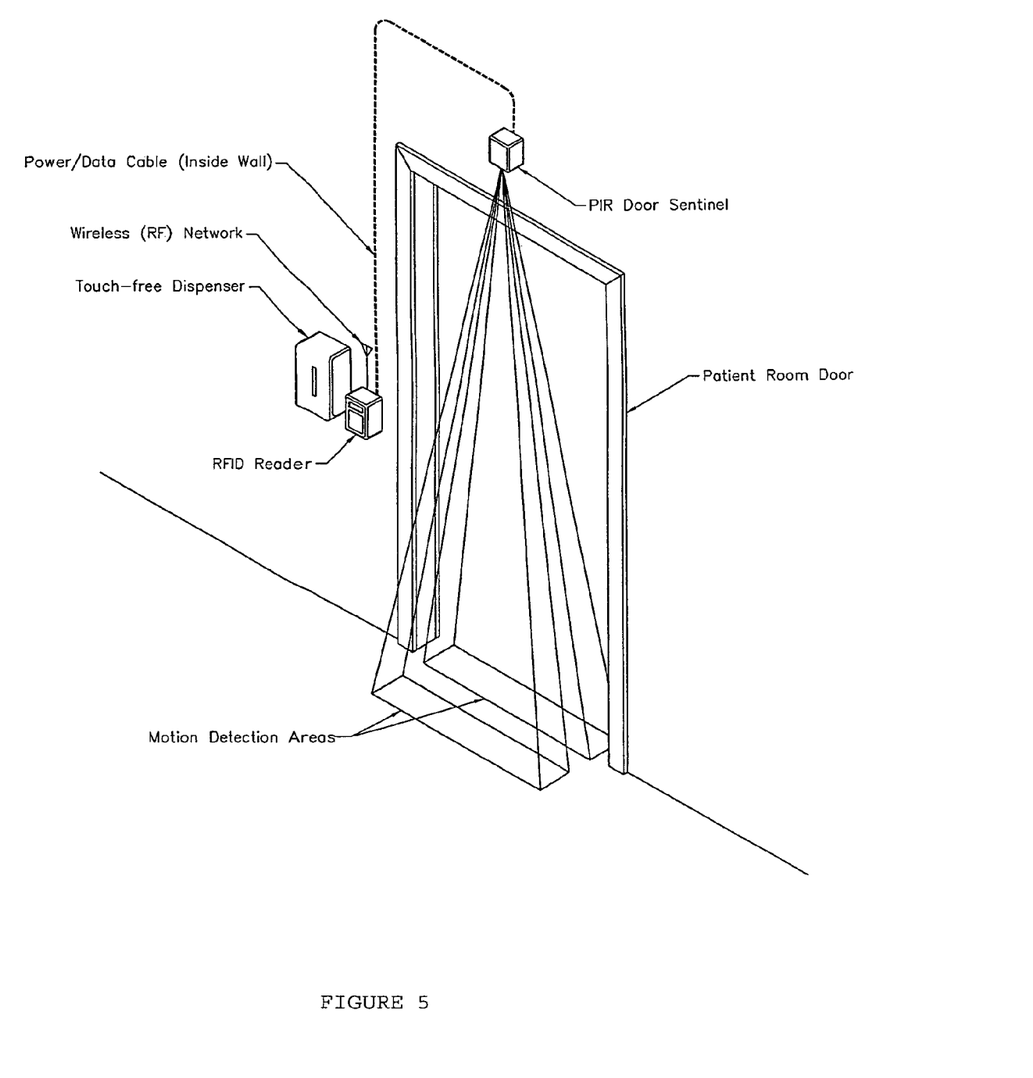
FIG. 5 shows an arrangement wherein the sensor is mounted above the patient room door to look down to the floor.

FIG. 5 shows an arrangement wherein the sensor is mounted above the patient room door to look down to the floor. This arrangement will effectively create a barrier much like a curtain. A Fresnel lens may be used.

PIR sensors can be divided into two regions; one that generates a positive signal when IR is detected and one that generates a negative signal when IR is detected. This dual sensor arrangement can be used to cancel out ambient IR sources in the environment. It also has the added benefit of allowing the system to determine the direction of a person passing through the doorway. PIR sensors also have a wide angle of coverage that is typically over 100°. A mechanical "eyelid" could be used that would allow the installer to custom fit the sensor's coverage to almost any door width. A PIR would simplify installation because no reflector is required. Having the sensor mounted above the door will reduce the likelihood that the sensor will be accidentally bumped or intentionally tampered with.

Although a preferred embodiment has been described, the invention is not limited to this embodiment and the scope of the invention is defined by the following claims.

APPENDIX A

DEVICE ID ASSIGNMENT

| Device | ID | Description |
|---|---|---|
| N/A | 0 | Broadcast to all device types |
| ProGiene G3 | 1 | ProGiene G3 touch-free group hand hygiene monitoring dispenser |
| ProSense Controller | 2 | ProSense touch-free faucet controller |
| RESERVED | 3 | Reserved for future use |
| ProGiene Data Logger | 4 | Hand held data logger for ProGiene G3 virtual network |
| Sensor T1 | 5 | Wireless sensor type 1 - contact closure event |
| Sensor T2 | 6 | Wireless sensors type 2 - multi-event with PC interface |
| Hub | 100 | Wireless hub/repeater |
| Gateway | 101 | Wireless gateway with embedded GSM modem |
| RESERVED | 250 | Reserved for future use |
| RESERVED | 251 | Reserved for future use |
| RESERVED | 252 | Reserved for future use |
| RESERVED | 253 | Reserved for future use |
| RESERVED | 254 | Reserved for future use |
| Master | 255 | Master device for master/slave RS-485 protocol |

APPENDIX B

EVENT ID ASSIGNMENT

| Event | ID | Description |
|---|---|---|
| RESERVED | 0 | Reserved for future use |
| Dispenser Activation | 1 | Contact closure - dispenser activation |
| Dispenser Cover Opened | 2 | Dispenser's cover was opened |
| Dispenser Cover Closed | 3 | Dispenser's cover was closed |
| Object Blocking IR | 4 | Object placed under dispenser within IR range |
| Object Blocking IR Removed | 5 | Object under dispenser within IR range removed |
| RESERVED | 250 | Reserved for future use |
| RESERVED | 251 | Reserved for future use |
| RESERVED | 252 | Reserved for future use |
| RESERVED | 253 | Reserved for future use |
| RESERVED | 254 | Reserved for future use |
| RESERVED | 255 | Reserved for future use |

The invention claimed is:

1. A monitoring and communication system for sanitize compliance monitoring comprising:

a detector for detecting the identity of a person;

a sanitizer monitoring sensor for collecting sanitizer compliance data at a sanitizer station, said sensor located to monitor and store sanitizer activation event data indicating whether a person passing through a portal has undergone a sanitization procedure and to store sanitizer activation event data for such procedures; and a wireless link for transmitting the sanitizer compliance data including sanitizer activation event data, wherein at least part of the link is over a cellular telephone network to a central monitoring station, the compliance data including the identity of the person passing through the portal and whether that person has undergone a sanitization procedure, wherein sanitizer activation event data can be buffered with a time offset during the time that data for another sanitizer activation event is transmitting.

2. The monitoring and communication system according to claim 1, wherein the monitoring sensor transmits sanitizer compliance data to a central hub before transmission over the cellular telephone network.

3. The monitoring and communication system according to claim 1, wherein the wireless link comprises a gateway which wirelessly receives the sanitizer compliance data from the monitoring sensor before transmission over the cellular telephone network.

4. The monitoring and communication system according to claim 2, comprising a plurality of hubs which wirelessly communicate to a gateway before transmission over the cellular network.

5. The monitoring and communication system of claim 1, further including a remote server and database store at the central monitoring station.

6. The monitoring and communication system of claim 5, further including an internet connection at the central station to enable internet access to the remote server and database store.

7. The monitoring and communication system of claim 1, including a plurality of hubs, wherein at least one hub of the plurality can receive sanitize compliance data transmitted from another hub, and retransmit the data.

8. The monitoring and communication system of claim 1, wherein the sensor comprises a passive RFID tag reader, to detect RFID tags worn by users.

9. The monitoring and communication system of claim 1, wherein the system includes a sanitizer dispenser.

10. The monitoring and communication system of claim 1, wherein the sensor comprises a sanitizer dispenser and detects whether the sanitizer dispenser has dispensed sanitizer within a time period before a person is detected passing through a portal, and produces a hygiene non-compliant, portal-passage event signal if sanitizer has not been dispensed during said time period.

11. The monitoring and communication system of claim 10, including an alarm which generates a signal in response to the hygiene non-compliant, portal-passage event signal.

12. The monitoring and communication system of claim 1, wherein the detector comprises an infrared detector to detect a person.

13. The monitoring and communication system of claim 1, wherein the detector comprises a laser for producing a laser beam.

14. The monitoring and communication system of claim 1, wherein the detector is mounted along the perimeter of the portal.

15. The monitoring and communication system of claim 1, comprising a plurality of sanitizer monitoring sensors for collecting sanitizer compliance data at a respective plurality of sanitizer stations.

16. A monitoring and communication system for sanitizer compliance monitoring, comprising:
    a detector for detecting the identity of a person;
    a sanitizer monitoring sensor for collecting sanitizer compliance data including sanitizer activation event data at a sanitizer station, said sensor located to monitor whether a person entering a door has undergone a sanitization procedure, said sensor transmitting the sanitizer activation event data, and a memory for buffering sanitizer activation event data with a time offset during the time that data for another sanitizer activation event is transmitted;
    at least one hub which wirelessly receives sanitizer compliance data transmitted from said sanitizer monitoring station, the compliance data including the identity of the person entering the door and whether that person has undergone a sanitization procedure;
    a gateway which wirelessly receives sanitizer compliance data transmitted from the hub; and
    a wireless cellular telephone link for transmitting the sanitizer compliance data from the gateway to a central monitoring station.

17. The communication system according to claim 16, comprising at least two hubs, each of which wirelessly receives sanitizer compliance data from a sanitizer monitoring sensor.

18. The communication system of claim 16, further including a remote server and database store at the central monitoring station.

19. The communication system of claim 18, further including an internet connection at the central station to enable internet access to the remote server and database store.

20. The communication system of claim 16, including a plurality of hubs, wherein at least one hub of the plurality can receive sanitize compliance data transmitted from another hub, and retransmit the data.

21. The monitoring and communication system of claim 16, wherein each sensor comprises a passive RFID tag reader, to detect RFID tags worn by users.

22. The monitoring and communication system of claim 16, wherein the system includes a sanitizer dispenser.

23. The monitoring and communication system of claim 16, wherein the sensor comprises a sanitizer dispenser and detects whether the sanitizer dispenser has dispensed sanitizer within a time period before a person is detected passing through a portal, and produces a hygiene non-compliant, portal-passage event signal if sanitizer has not been dispensed during said time period.

24. The monitoring and communication system of claim 23, including an alarm which generates a signal in response to the hygiene non-compliant, portal-passage event signal.

25. The monitoring and communication system of claim 16, wherein the detector comprises an infrared detector to detect a person.

26. The monitoring and communication system of claim 16, wherein the detector comprises a laser for producing a laser beam.

27. The monitoring and communication system of claim 16, wherein the detector is mounted along the perimeter of the portal.

28. The monitoring and communication system of claim 16, comprising a plurality of sanitizer monitoring sensors for collecting sanitizer compliance data at a respective plurality of sanitizer stations.

29. A method for monitoring and communicating sanitizer compliance data, comprising:
    detecting the identity of a person;
    collecting sanitizer compliance data from a sanitizer station having a monitoring sensor, the compliance data including data of a sanitization activation event indicating the identity of the person and when that person has undergone a sanitization procedure;
    transmitting the collected sanitizer compliance data wirelessly, wherein at least part of the transmission is over a cellular telephone network to a central monitoring station; and
    storing in memory sanitization activation event data and a time offset for an activation event while data for a prior sanitization event is being transmitted.

30. The method of claim 29, including the step of wirelessly transmitting the sanitizer compliance data from the sanitizer station to a central hub, before transmitting the data wirelessly over the cellular network.

31. The method of claim 29, including using a gateway which wirelessly receives the sanitizer compliance data from the sanitizer monitoring sensor before transmission over the cellular telephone network.

32. The method of claim 29, including transmitting the data wirelessly over a plurality of hubs to a gateway before transmission over the cellular network.

33. The method of claim 29, including providing a remote server and database store at the central monitoring station.

34. The method of claim 29, including providing an internet connection at the central station to enable internet access to the remote server and database store.

35. The method of claim 29, including providing a plurality of hubs, wherein at least one hub of the plurality receives sanitize compliance data transmitted from another hub, and retransmits the data.

36. The method of claim 29, comprising using a passive RFID tag reader to detect RFID tags worn by users.

37. The method of claim 29, further comprising providing a sanitizer dispenser.

38. The method of claim 29, comprising detecting whether a sanitizer dispenser has dispensed sanitizer within a time period before a person is detected passing through the portal, and providing a hygiene non-compliant, portal-passage event signal if sanitizer has not been dispensed during said time period.

39. The method of claim 38, including producing an alarm signal in response to a hygiene non-compliant, portal-passage event signal.

40. The method of claim 29, comprising using an infrared detector.

41. The method of claim 29, comprising locating a detector along the perimeter of the portal.

42. A monitoring and communication system for sanitize compliance monitoring comprising:
- a detector for detecting the identity of a person;
- a sanitizer monitoring sensor for collecting sanitizer compliance data at a sanitizer station, said sensor located to monitor whether a person passing through a portal has undergone a sanitization procedure, said sensor having a cover which opens and closes, and a battery, and also collecting sensor event conditions including at least one of cover closed, low battery, and whether the sensor is blocked by an object; and
- a wireless link for transmitting the sanitizer compliance data and sensor event conditions data over a cellular telephone network to a central monitoring station, the compliance data including the identity of the person passing through the portal and whether that person has undergone a sanitization procedure.

43. A monitoring and communication system for sanitize compliance monitoring comprising:
- a detector for detecting the identity of a person;
- a sanitizer monitoring sensor for collecting sanitizer compliance data at a sanitizer station, said sensor located to monitor whether a person passing through a portal has undergone a sanitization procedure; and
- a hub which receives sanitizer compliance data from the monitoring sensor; and
- a wireless link for receiving sanitizer compliance data from the hub and transmitting the sanitizer compliance data over a cellular telephone network to a central monitoring station, the compliance data including the identity of the person passing through the portal and whether that person has undergone a sanitization procedure, said sensor buffering sanitizer activation event data with a time offset during the time that data for another sanitizer activation event is being transmitted, and wherein the hub creates a time-date stamp indicating when the activation event is received and adjusts the time-date stamp of occurrence of the activation event.

\* \* \* \* \*